(12) United States Patent
Licklider et al.

(10) Patent No.: US 6,989,129 B2
(45) Date of Patent: Jan. 24, 2006

(54) AUTOMATED CAPILLARY LIQUID CHROMATOGRAPHY SMALL VOLUME ANALYSIS SYSTEM

(75) Inventors: Lawrence J. Licklider, Jamaica Plain, MA (US); Steven P. Gygi, Foxboro, MA (US); Junmin Peng, Brighton, MA (US)

(73) Assignee: The President and Fellows of Harvard College, Cambridge, MA (US)

(*) Notice: Subject to any disclaimer, the term of this patent is extended or adjusted under 35 U.S.C. 154(b) by 631 days.

(21) Appl. No.: 10/115,692

(22) Filed: Apr. 4, 2002

(65) Prior Publication Data

US 2002/0146349 A1 Oct. 10, 2002

Related U.S. Application Data

(60) Provisional application No. 60/281,612, filed on Apr. 5, 2001.

(51) Int. Cl.
*G01N 30/02* (2006.01)
*G01N 30/08* (2006.01)

(52) U.S. Cl. .................. 422/70; 73/61.53; 73/61.55; 73/61.56; 73/61.58; 210/198.2; 210/656; 422/101; 436/161

(58) Field of Classification Search .............. 210/198.2, 210/656; 422/70, 101; 436/161; 73/61.53, 73/61.55, 61.56, 61.58
See application file for complete search history.

(56) References Cited

U.S. PATENT DOCUMENTS 4,454,749 A * 6/1984 Guillemin et al. ......... 73/23.39
5,135,549 A * 8/1992 Phillips et al. ................ 95/8
6,001,229 A * 12/1999 Ramsey .................... 204/451
6,139,734 A * 10/2000 Settlage et al. .......... 210/198.2

* cited by examiner

*Primary Examiner*—Jan M. Ludlow
(74) *Attorney, Agent, or Firm*—Charles G. Call

(57) ABSTRACT

A system for automatically performing liquid chromatography analysis of low volume liquid chemical samples at nanosecond flow rates using an analysis column that integrates a pre-concentration trapping column and a chromatography separation column terminating at an electrospray nozzle of an online mass spectrometer. The analysis column consists of a capillary having an inside diameter of between 75 and 125 microns packed throughout with a porous bed of micron particles. A branch outlet positioned 10 to 16 centimeters upstream from the nozzle divides the analysis column into an upstream pre-concentration trap and a downstream separation column. An autosampler delivers low volume liquid samples to the upstream inlet via a two-position valve. Feed connections couple the autosampler to upstream inlet when the valve is open to inject a liquid sample into the pre-concentration trap at a maximum loading flow rate in the range from 0.5 to 50 microliters/minute. Thereafter, when the valve closes, it terminates the further injection the sample, and a concentrated portion of the sample then passes though the chromatography separation column at a much slower flow rate between 10 and 1,000 nanoliters per minute. Throughput can be doubled by coupling two such analysis columns to a single autosampler using a ten-port, two position valve. A single column can be supplied through a six port two-position valve.

20 Claims, 4 Drawing Sheets

AUTOMATED CAPILLARY LIQUID CHROMATOGRAPHY SMALL VOLUME ANALYSIS SYSTEM

CROSS-REFERENCE TO RELATED APPLICATION

This application claims the benefit of the filing date of the copending U.S. Provisional Patent Application Ser. No. 60/281,612 filed by applicants on Apr. 5, 2001.

FEDERALLY SPONSORED RESEARCH

This invention was made by an agency of the U.S. Government, or under a contract for an agency of the U.S. Government. The name of the agency of the U.S. Government and the contract number is:

National Institutes of Health, U.S. Dept. of Health and Human Services Grant HG00041

FIELD OF THE INVENTION

This invention relates to methods and apparatus for performing biochemical analysis and more particularly to the automation of capillary liquid chromatography—mass spectrometry/mass spectrometry (LC-MS/MS) systems operating at very low flow rates.

BACKGROUND OF THE INVENTION

There is a need to automate capillary LC/MS systems for use in applications which require pre-concentration. Prior automated $\mu$LC/MS/MS systems employ trapping/pre-concentration columns integrated with the separation column through transfer lines. However, the integration of the trap with an analysis column which operates at very low flow rates (200 nanoliters per minute and less) presents special challenges.

Capillary LC-MS/MS systems operating at very low flow rates can be automated by using an autosampler to load a peptide trap at higher flow rates in the range from 0.5 to 500 microliters per minute, and preferably in the range from 5- to 50 microliters per minute. After washing, a valve connects the trap on-line with the LC column at a slower rate from 10 to 1,000 nanoliters per minute, and preferably at about 200 nanoliters per minute. An on-line mass spectrometer is used to detect the chromatography eluent from the analysis column. While this technique has been automated, the resulting systems have been characterized by large extra-column volumes and other problems.

BRIEF SUMMARY OF THE INVENTION

It is an object of the present invention to provide improved methods and apparatus for automating a capillary LC-MS/MS system operating at very low flow rates.

The present invention takes the form of a microcapillary-based chemical analysis system designed for nanoliter-scale analysis of microliter-scale samples. The present invention alters the position and nature of the sample enrichment trap to obtain improved performance.

The present invention alters the magnitude and direction of fluid motion within the microcapillary bed. This alteration allows a single bed to have improved performance in sample enrichment and in the removal of a range of soluble contaminants.

The present invention greatly lessens dilutions effects by eluting the trap into the remainder of the analysis column via a microscale union (tee or cross) wherein the direction and the magnitude of fluid flow can be controlled by an external 2-position valve. We call this configuration "V-Column" to connote the vent flow from the union via its connection to the open position on the valve." The configuration has also been termed a "TRALUMN" to connote the direct fusion of the TRAp and the coLUMN.

In the specific embodiment of the invention to be described, a 100 or 75 micron fused-silica microcapillary analytical column terminating at a needle tip is packed throughout with a 15 cm bed of bed of $C_{18}$ bonded phase particles having a 5 micron particle size and a 200 Å pore size. A mass spectrometer monitors the effluent from the column at the tip. A low-volume cross, also packed with $C_{18}$ particles, is inserted into the microcapillary column about 12 cm upstream from the needle tip. One arm of the two remaining arms of the cross receives an electrical conductor to which a high voltage is applied for the electrospray. The fourth row of the packed cross is coupled to a separate, fritted 50–500 micron capillary connected to a two-position valve. The frit can be positioned inside or outside the second capillary.

When the two-position valve is open, the section of the column upstream from the cross is loaded at 0.5–10 microliters/minute by an autosampler. When the two-position valve is closed, the sample is permitted to flow at a much lower flow rate of about 200 nanoliters per minute through the 12 cm packed capillary column downstream from the cross to the electrospray tip at the mass spectrometer inlet.

As contemplated by the invention, the fusion of a high flow rate (microliter per minute) pre-concentration column which forms the trap with a much slower (nanoliter per minute) flow rate analysis column permits the samples to be automatically introduced with improved sample throughput and reproducibility without sacrificing either the performance or the sensitivity for the analysis column.

These and other objects, features and advantages of the present invention may be more clearly understood by considering the following detailed description of a specific embodiment of the invention. In the course of this description, frequent reference will be made to the attached drawing.

DETAILED DESCRIPTION

Figure 1:
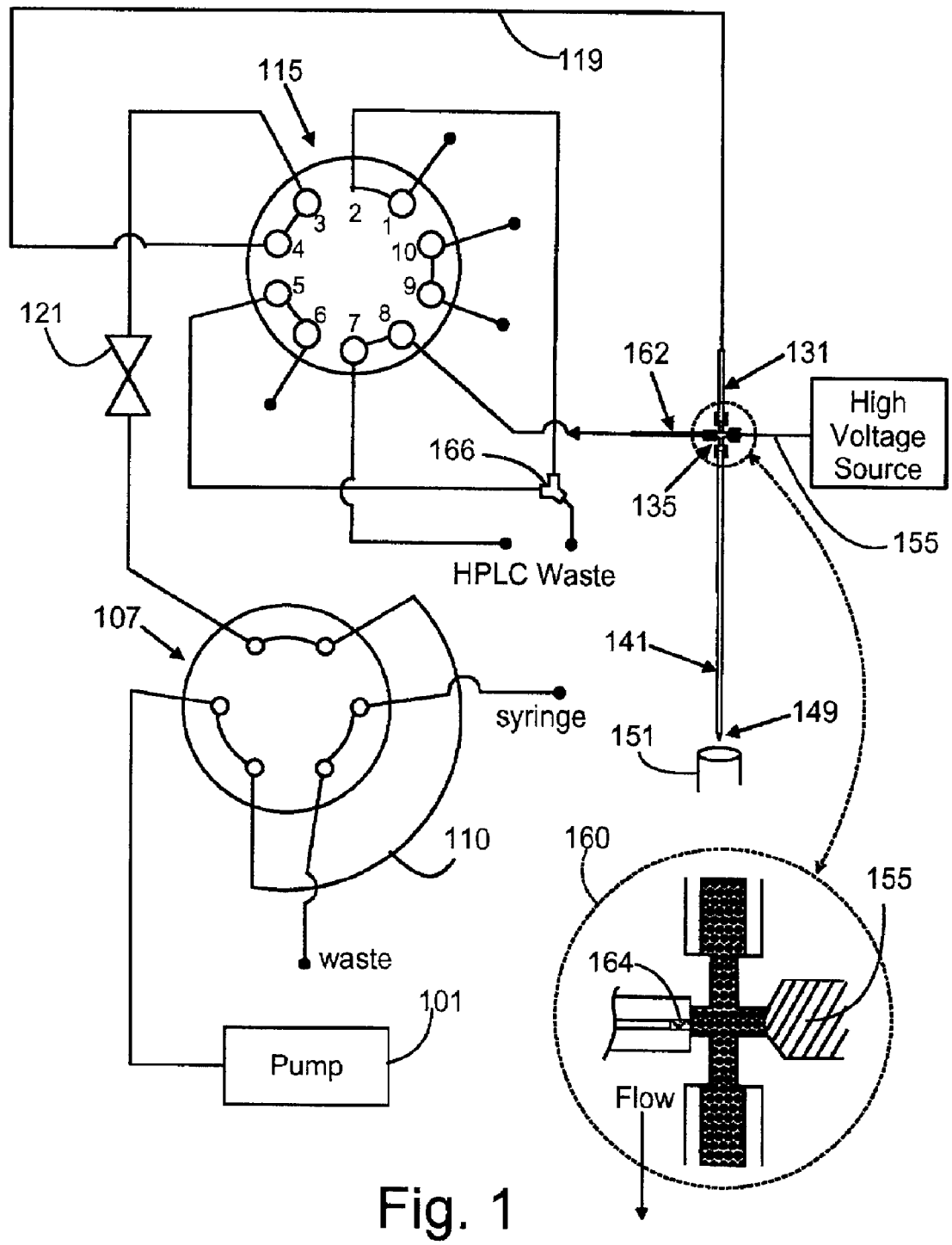
FIG. 1 is a schematic diagram illustrating fluid flow pathways in the preferred embodiment with the valve in the open position.

The greatest sensitivity for structural characterization or identification of biomolecules can be obtained by performing liquid chromatography (LC) analyses at low nanoliter flow rates using on-column sample-loading, separation, and detection. At these flow rates an analysis column of 100 micron or smaller diameter is utilized to provide chromatography fractions on the order of 200 nL and smaller. To allow on-column analyte enrichment and to utilize larger sample volumes, typically 1 to 100 microliters, the column consists of a porous bed which promotes retention of analytes during the sample loading step. To allow automated liquid sample-handling stations (autosamplers) to perform the loading step, a short column must be used which permits a maximum flow rate in the range from 0.5 to 50 microliters/minute, and preferably between 5 and 50 microliters/min, while samples are transferring to the column (trap) and to allow non-retained solutes to be washed from the trapping column. During the separation step, analytes are eluted from the trap and transfer in the mobile phase to a full-length separation column. The trap cross-sectional area, as well as, extra-column volume must be minimal due to the low elution flow rates since any dilution will have adverse effects on the detection sensitivity, as well as, on the separation column performance. The present invention greatly lessens dilution effects by miniaturizing the trapping column and directly fusing it with the separation column. In the specific embodiment of the invention described here, a 100 or 75 micron fused-silica capillary was packed throughout with a 15 cm bed of $C_{18}$ bonded phase particles having a 5 micron particle size and a 200 Å pore size. The column was then cut at between 13 and 14 cm and a low-volume tee or cross-union was inserted. The arm of the union attached to a two-position valve contains a fritted 50–150 micron ID capillary located immediately before the port opening as illustrated in FIG. 1 and discussed in more detail below.

Large sample volumes from an autosampler were loaded across the short column segment with the valve in the open position at 5–10 microliters/min. Flow rates during loading and during an optional wash step were limited by analyte retention characteristics and the flow impedance, respectively, each being constrained by the length and the porosity chosen for the short bed. Closing the valve permitted flow rates of 200 nanoliters per minute or lower to pass over the short segment and through the separation column. Detection of the peak fractions eluting from the separation column was done by electrospray mass spectrometry (ESI-MS). The voltage application for ESI was done on-column either at one arm of the cross-union, or at another low-volume tee-union which either segmented the separation column at the outlet end or which united the outlet with a short 3 to 4 cm length capillary of 20 micron diameter having a needle tip. LC/ESI-MS/MS analyses of peptides have been fully automated with a Surveyor autosampler (ThermoFinnigan) and an LCQ DECA ion trap MS (ThermoFinnigan). Analysis of standard peptides, protein digests, and in-gel protein digests were performed using the V-column approach. The sensitivity was found to be at the low fmol level. Unknown proteins from silver-stained gel bands were automatically identified by searching tandem mass spectra against sequence databases using the Sequest algorithm.

The basic components of an automated $\mu$LC/MS/MS which utilizes the invention are shown in FIG. 1. The system consists of a pump 101 which delivers the solvent (or mobile phase) to an autosampler 107 which then delivers samples from the loop 110 to a two-way, ten-port valve 115. When the valve 115 is in the open position shown in FIG. 1, a sample flows at a relative high flow rate from the autosampler 107 through a PEEK filter 121 to the valve 115 and then through a 50 $\mu$m i.d. fused silica capillary 119 to the upstream end of a section 131 of a packed microcapillary analytical column. Two opposing arms of a packed cross at 135 couple the upstream section 131 to a 12 cm long downstream section 141 of the microcapillary column. The distal end of the downstream analysis column section 141 forms a needle tip 149 for the electrospray which passes to the inlet 151 of a mass spectrometer. The third arm of the cross 135 receives a gold wire 155 (best seen in the enlarged view of the cross at 160). The fourth arm of the cross 135 is connected to the two-position valve 115 by a 50 $\mu$m i.d. fused silica capillary 162 with a frit 164 at connection to the cross 135. Frit 164 can be any porous material that can protect the packing of the column from exiting. The frit is positioned to prevent the vent arm of the tee or cross from receiving the bed when pressure is applied to the bed. The frit can be placed in either the port connection on the trap arm or the port connection on the vent arm. Putting it in the trap arm avoids the necessity to fill the tee or cross union with the bed particles. In this embodiment, 10 micrometer silica beads are used.

Figure 2:
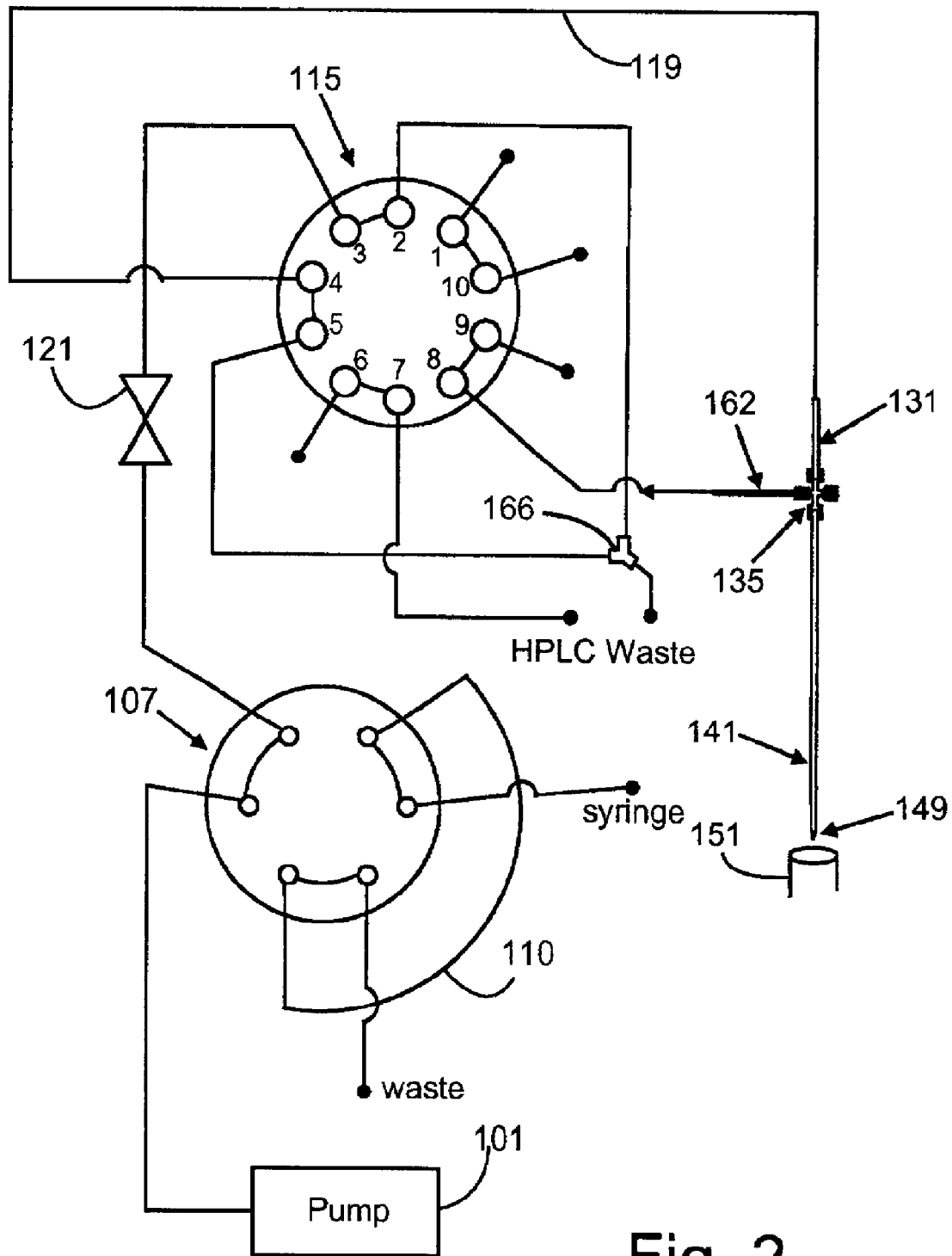
FIG. 2 is a schematic diagram illustrating the fluid flow pathways when the valve is in the closed position.

As shown in FIG. 2, when the two-position valve 115 is switched to the closed position, the output of the autosampler 107 is disconnected from the column feed tube 119. The feed tube 119 is instead connected to the HPLC waste outlet through a flow splitter 166. Similarly, the fritted tube 162 which formerly connected the cross 135 to the HPLC waste outlet is disconnected. In the closed position shown in FIG. 2, a much lower flow rate of about 200 nanoliters per minute is permitted through the 12 cm packed capillary column 141 downstream from the cross 135 to the electrospray tip 149 and the mass spectrometer inlet 151.

The present invention achieves a significant improvement in performance by reducing the dead-volume which would otherwise be present by connecting the trap directly to the remainder of the analysis column using a small-volume bi-directional flowpath which operates under the control of the external valve. This principle may be applied generally to control the direction, magnitude, and the composition of fluid flow at desired point(s) within a microscale chromatography bed to provide cross-flow addition of fluids to the bed, to isolate downstream segments of the bed, and to introduce voltage gradients in the bed for electrophoretic separations. It should be recognized that the improved performance resulting from the elimination of dead volume is distinct from and adds to the advantages achieved by using such a small-volume union and external valve to elute the trap segment directly into the column.

Components

The method and apparatus described above has been used to fully automate the analysis of 96-, 384-, or other, multi-well plates. A Surveyor MS Pump available from ThermoFinnigan of San Jose, Calif. that is designed for optimal performance at the low flow rates used with mass spectrometry was used with a Surveyor Autosampler, also available from ThermoFinnigan. The output of the analysis column was detected by a ThermoFinnigan model LCQ DECA, an ion trap mass spectrometer supplied with a Finnegan Electrospray (ESI) ionization source. The ThermoFinnigan Xcalabur™ software provided with the LCQ DECA mass spectrometer provides data reduction and display capabilities.

The two-position valve 115 may be implemented using a 10 port model C2 sampling and switching valve available from Valco Instruments Co. Inc. of Houston, Tex.

The upstream and downstream sections 131 and 141 of the analysis column consist of 75–100 $\mu$m i.d. fused silica capillary tubing packed with a bed of $C_{18}$ bonded phase particles having a 5 micron particle size and a 200 Å pore size. The cross 135 is similarly packed with the $C_{18}$ particles. The analysis column may be packed with ion-exchange, size-exclusion, gel filtration affinity, or other media of choice. Any combination of media in various configurations can also be used. The upstream section 131 above the cross 135 is 1–2 centimeters long and the downstream section is 12 centimeters long.

Figure 3:
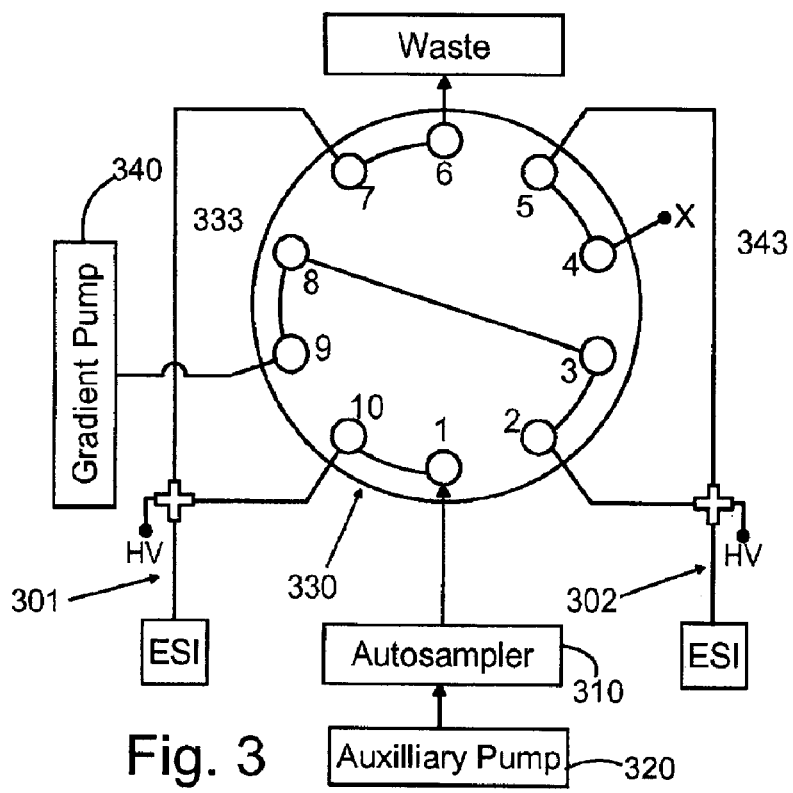
FIGS. 3 and 4 are schematic diagrams illustrating two columns that operate concurrently to improve the throughput of the system.
Figure 4:
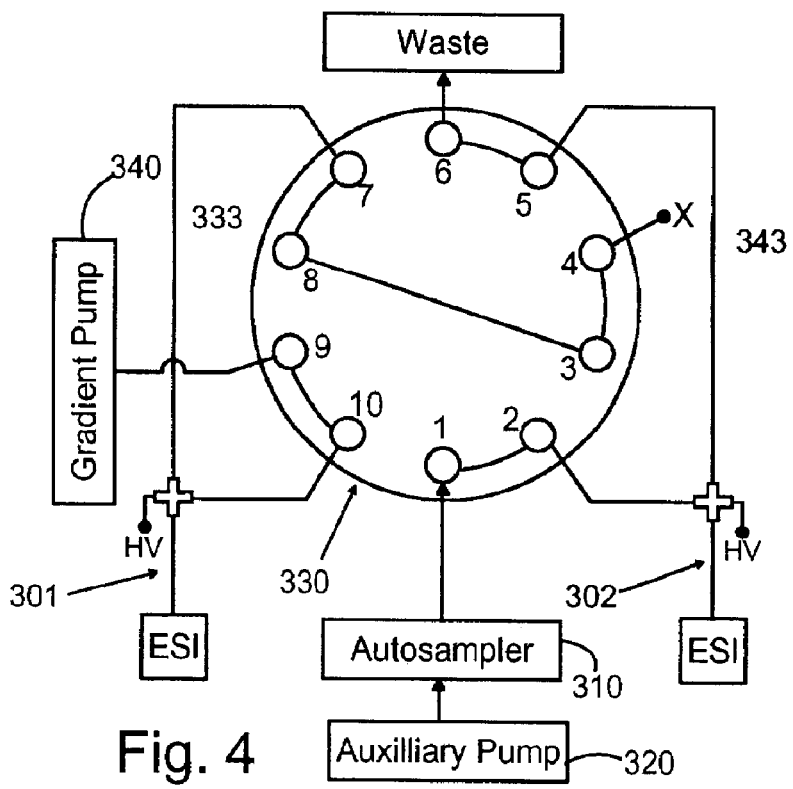

The throughput of the system using the invention may be multiplied by using more than one column at the same time as illustrated by the two-column arrangement shown in FIGS. 3 and 4 of the drawings.

In this arrangement, a first column indicated generally at 301 and a second column indicated generally at 302 are both connected to a single autosampler 310 and pump 320 by a two-position, 10-port valve 330.

When the valve 330 is in the first position shown in FIG. 3, the output of the autosampler 310 is connected to feed the analysis column 301. At this time, the valve 330 also connects a fritted capillary tube 333 coupled to the first column 301 to a waste outlet 335. In this first position, the valve 330 also connects a gradient pump 340 to load and wash the second column 302.

In its second position illustrated in FIG. 4, the valve 330 connects the output of the autosampler 310 to the second column 302 while, at the same time connecting the output of the gradient pump 340 to the first column 302 and connecting the fritted capillary tube 343 to the waste outlet 335. As illustrated in FIGS. 3 and 4, throughput is doubled by running two analysis columns simultaneously with one column loading and washing while the other is running a sample.

Figure 5:
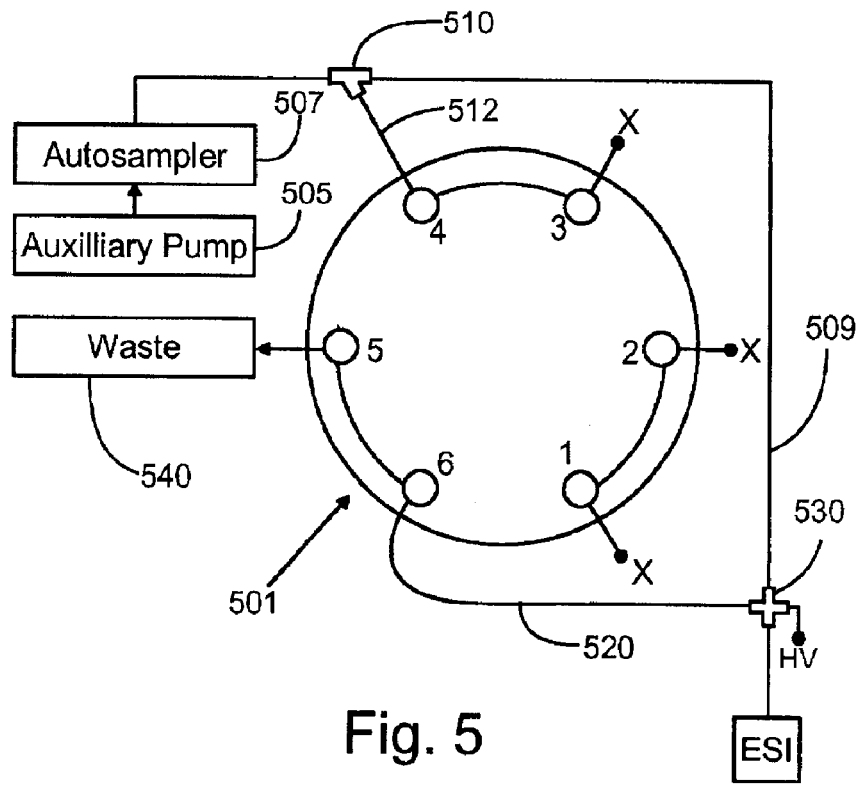
FIGS. 5 and 6 are schematic diagrams showing an alternative embodiment employing a six-port valve.
Figure 6:
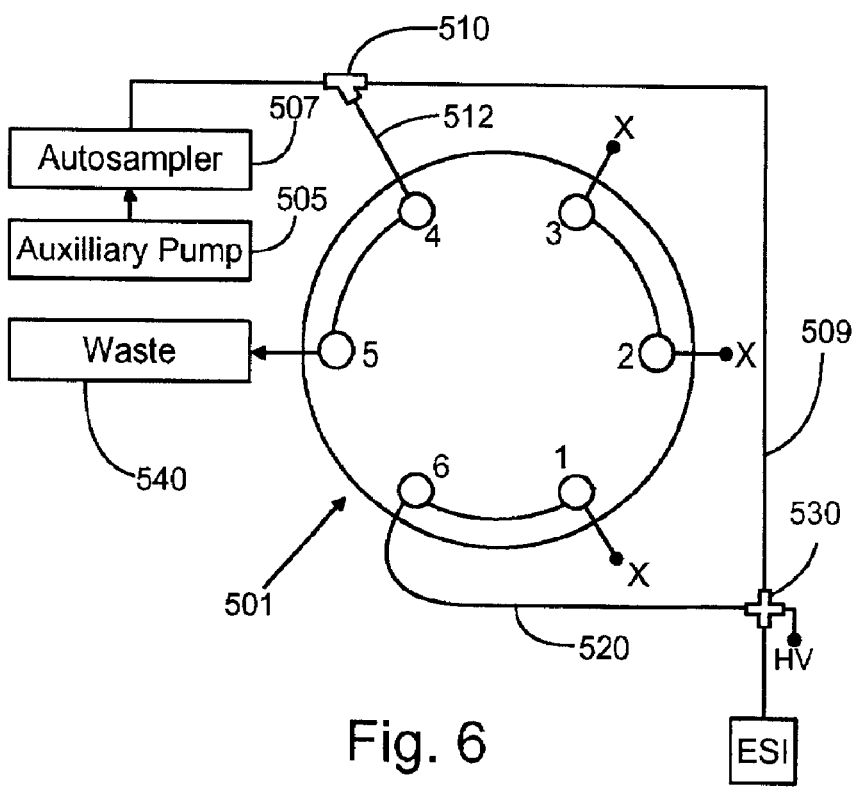

The arrangement shown in FIGS. 5 and 6 may be used to advantage to reduce the component cost and complexity of the analysis apparatus when a single V-column is used.

This single V-column is implemented using a six-port valve 501 as shown in FIGS. 5 and 6. A pump 505 and an autosampler 507 are connected to load the upper trap section 509 of the analysis column via a flow splitter (T-union) seen at 510. With the six port valve 501 in position shown in FIG. 5, the other output branch 512 from the flow splitter 510 is closed and the fritted capillary 520 from the cross 530 is connected to an open waste outlet 540.

Switching the valve 501 to the other position as shown in FIG. 6 closes the fritted capillary arm 520 and connects the branch 512 to the open waste outlet 540. In this position, the flow splitter 510 regulates the flow rate.

Conclusion

It is to be understood that the embodiments of the invention that have been described are merely illustrative of applications of the principles of the invention. Numerous modifications may be made to the arrangements described without departing from true spirit and scope of the invention.

What is claimed is:

1. An automatic capillary liquid chromatography chemical analysis system comprising, in combination,
    a capillary defining a fluid passageway having an inlet end, and outlet end, and an intermediate branch outlet, said capillary being filled with a porous material to form a trapping pre-concentration column between said inlet end and said intermediate branch outlet and a separation column between said branch outlet and said outlet end,
    loading flow control means coupled to said inlet end and to said branch outlet for passing a liquid sample through said trapping pre-concentration column,
    analysis flow control means for terminating the further introduction of said liquid sample into said pre-concentration column via said inlet end and for thereafter passing a concentrated liquid sample from said pre-concentration column through said separation column at a separation flow rate between 10 and 1,000 nanoliters per minute to deliver chromatography eluent through said outlet end, and
    an analyzer positioned at said outlet end for receiving and analyzing said chromatography eluent delivered from said separation column via said outlet end.

2. The system according to claim 1 wherein said loading flow control means limits the maximum loading flow rate of said liquid sample through said trapping pre-concentration column to between 0.5 and 50 microliters/minute.

3. The system according to claim 1 wherein said separation flow rate is between 100 and 300 nanoliters per minute.

4. The system according to claim 2 wherein said separation flow rate is between 100 and 300 nanoliters per minute.

5. The system according to claim 1 wherein said analyzer is a mass spectrometer.

6. The system according to claim 4 wherein said analyzer is a mass spectrometer.

7. The system as set forth in claim 5 including electrical contact means coupled to said capillary and to a voltage source for applying an electrical potential to create an electrospray of said chromatography eluent delivered via said outlet end to said mass spectrometer.

8. The system as set forth in claim 1 wherein said porous material is a bed of $C_{18}$ bonded phase particles having a 5 micron particle size and a 200 Å pore size.

9. The system as set forth in claim 5 wherein said porous material is a bed of $C_{18}$ bonded phase particles having a 5 micron particle size and a 200 Å pore size.

10. The system as set forth in claim 1 wherein said loading flow control means comprises an automatic sample loader for delivering a succession of liquid samples through said inlet end to said trapping pre-concentration column.

11. The system as set forth in claim 10 wherein said loading flow control means includes a second capillary having an inside diameter between 50 and 500 microns connected to said branch outlet to carry a flow of said liquid sample from said trapping pre-concentration column.

12. The system as set forth in claim 10 further including a frit positioned at said branch outlet to prevent said porous material from passing from said capillary through said branch outlet.

13. The system as set forth in claim 1 wherein said capillary has an inside diameter between 50 and 150 microns.

14. A system for automatically analyzing a plurality of liquid chemical samples comprising, in combination,
    a first capillary having an inside diameter of between 50 and 150 microns packed with a porous bed of particles to form an analysis column having an upstream inlet, a downstream outlet, and a branch outlet positioned between said inlet and said outlet at a distance between 10 and 16 centimeters from said outlet, said analysis column forming a pre-concentration trap between said upstream inlet and said branch outlet and forming a chromatography separation column between said branch outlet and said downstream outlet,
    a mass spectrometer positioned to receive chromatography eluent from said downstream outlet,
    an autosampler for delivering said plurality of liquid samples,
    a two-position valve having an open position and a closed position, and
    feed connections coupling said autosampler to said upstream inlet via said two-position valve for injecting one of said liquid samples into said pre-concentration trap via said upstream inlet at a maximum loading flow rate in the range from 0.5 to 50 microliters/minute when said two-position valve is in said open position, for thereafter terminating the further injection of said one of said liquid samples via said upstream inlet when said two-position valve moves to said closed position, and for permitting the passage of a concentrated portion of said one of said liquid samples though said chromatography separation column at a lower flow rate between 10 and 1,000 nanoliters per minute to thereby deliver chromatography eluent through said downstream outlet to said mass spectrometer when said two position valve is in said closed position.

15. The system according to claim 1 wherein said maximum loading flow rate is between 5 and 50 microliters/minute and said lower flow rate is between 100 and 300 nanoliters per minute.

16. The system as set forth in claim 15 including a voltage source for applying an electrical potential to said downstream outlet produce an electrospray of said chromatography eluent directed to said mass spectrometer.

17. The system as set forth in claim 1 wherein said porous bed of particles comprises a bed of bonded phase particles having a particle size of about 5 microns.

18. The system as set forth in claim 10 wherein said feed connections include a second capillary having an inside diameter between 50 and 500 microns connected to said branch outlet to carry a flow of said liquid sample from said pre-concentration trap.

19. A system for automatically analyzing a plurality of liquid chemical samples comprising, in combination, first and second analysis columns each of which comprises a capillary having an inside diameter of between 50 and 150 microns packed with a porous bed of particles to form an analysis column having an upstream inlet, a downstream outlet, and a branch outlet positioned between said inlet and said outlet at a distance between 10 and 16 centimeters from said outlet, said analysis column forming a pre-concentration trap between said upstream inlet and said branch outlet and forming a chromatography separation column between said branch outlet and said downstream outlet, and a mass spectrometer positioned to receive chromatography eluent from said downstream outlet of each of said analysis columns an autosampler for delivering said plurality of liquid samples, a valve having first and second positions, a first set of feed connections coupling said autosampler to said upstream inlet of first analysis column via said two-position valve for injecting a second one of said liquid samples into the pre-concentration trap of said first analysis column via said upstream inlet of said first analysis column at a maximum loading flow rate in the range from 0.5 to 50 microliters/minute when said two-position valve is in said first position, for thereafter terminating the further injection of said first one of said liquid samples via said upstream inlet of said first analysis column when said two-position valve moves from said first to said second position, and for permitting the passage of a concentrated portion of said first one of said liquid samples though said chromatography separation column of said first analysis column at a lower flow rate between 10 and 1,000 nanoliters per minute to thereby deliver chromatography eluent derived from said first one of said liquid samples to said mass spectrometer positioned to receive chromatography eluent from said downstream outlet of said first analysis column when said two position valve is in said second position.

20. A system as set forth in claim 19 wherein said two position valve is a ten port two position valve.

* * * * *